United States Patent [19]
Davankov et al.

[11] Patent Number: 6,159,377
[45] Date of Patent: *Dec. 12, 2000

[54] METHOD OF PURIFICATION OF PHYSIOLOGICAL LIQUIDS OF ORGANISM

[75] Inventors: Vadim Davankov; Maria Tsyurupa; Ludmila Pavlova; Dzirda Tur, all of Moscow, Russian Federation

[73] Assignee: Renal Tech International LLC, New York, N.Y.

[*] Notice: This patent is subject to a terminal disclaimer.

[21] Appl. No.: 09/184,166

[22] Filed: Nov. 2, 1998

Related U.S. Application Data

[62] Division of application No. 09/019,584, Feb. 6, 1998.

[51] Int. Cl.$^7$ ................................................. B01D 15/00
[52] U.S. Cl. ............................................ 210/690; 210/767
[58] Field of Search .............................. 502/402; 521/30, 521/31, 32, 55, 75, 905, 918, 146; 428/305.5, 409, 543; 210/767, 690

[56] References Cited

U.S. PATENT DOCUMENTS

| | | | |
|---|---|---|---|
| 4,908,405 | 3/1990 | Bayer et al. | 525/61 |
| 5,037,857 | 8/1991 | Maroldo et al. | 521/29 |
| 5,079,274 | 1/1992 | Schneider et al. | 521/146 |
| 5,683,800 | 11/1997 | Stringfield et al. | 428/318.4 |
| 5,773,384 | 6/1998 | Davankov et al. | 502/402 |

*Primary Examiner*—Blaine Copenheaver
*Attorney, Agent, or Firm*—I. Zborovsky

[57] ABSTRACT

A method of purification of physiological liquids of organism has the step of passing a physiological liquid through a material which has a size, a shape, and a structure selected so as to remove toxic compounds from the physiological liquid and is composed of a partially chloromethylated porous highly crosslinked styrene or divinylbenzene copolymer which initially have surface exposed chloromethyl groups in which thereafter chlorine is replaced with an element which forms different surface exposed functional groups with a greater hydrophilicity and greater biocompatibility than that of the chloromethyl group.

7 Claims, No Drawings

METHOD OF PURIFICATION OF PHYSIOLOGICAL LIQUIDS OF ORGANISM

CROSS REFERENCE TO A RELATED APPLICATION

This application is a division of application Ser. No. 09/019,584 filed on Feb. 6, 1998, now allowed.

BACKGROUND OF THE INVENTION

The present invention relates to a method of purification of physiological liquids of organism.

It is well known that physiological liquids of organisms such as blood, plasma, peritoneal liquid etc., accumulate and transport various toxicants in the case of poisoning the organism as well as in the case of diseases, in particular diseases of liver and kidneys. It is therefore advisable to remove the toxicants from the physiological liquids to significantly improve the situation of the patient. A plurality of methods have been invented and have been utilized for removing toxicants from blood, plasma and other physiological liquids. One of the most efficient methods is hemodialysis. This method, however, is generally restricted to removing small toxic molecules, whereas toxins belonging to the so-called middle-size molecules (between 500 and 30000 Dalton molecular weight) are eliminated too slowly, even with modern "high flux" dialyser membranes. It is believed to be advisable to further improve the existing methods so as to provide an efficient purification of the physiological liquid of organism, especially with respect to above toxicants having larger molecular sizes, for the purpose of preventing propagation of diseases or curing the disease. Some solutions were disclosed in our earlier U.S. Pat. No. 5,773,384.

SUMMARY OF THE INVENTION

Accordingly, it is an object of present invention to provide a method of purification of physiological liquids of organism.

In accordance with the present invention, the method of purification of physiological liquids of organism comprises removing a physiological liquid containing toxicants from a patient, passing the physiological liquid through a material which has a size, a shape, and a structure selected so as to remove toxic compounds from the physiological liquid and is composed of a partially chloromethylated porous highly crosslinked styrene or divinylbenzene copolymer which initially have surface exposed chloromethyl groups in which thereafter chlorine is replaced with an element which forms different surface exposed functional groups with a greater hydrophilicity and greater biocompatibility than that of the chloromethyl group.

In accordance with a preferable embodiment of the present invention, the pore size of the material is selected as being in the range between 1 and 15 nm and the structure of the material is selected such that hydrophobic surface in the above pores should be exposed to middle-size molecules. Thus, hydrophobic microporous and mesoporous polymeric materials are best suited for removing toxicants such as for example beta2 microglobulin and others. These materials may also contain transport-enhancing macropores which surface, however, must be made biocompatible, just like the other surface of the polymer material.

When the method is performed in accordance with present invention, it provides for an efficient removal of broad range of toxicants from blood, plasma and other physiological liquids of organism.

The novel features which are considered as characteristic for the present invention are set forth in particular in the appended claims. The invention itself, however, both as to its construction and its method of operation, together with additional objects and advantages thereof, will be best understood from the following description of specific embodiments.

DESCRIPTION OF PREFERRED EMBODIMENTS

In accordance with present invention, a purification of physiological liquids of organism by removing toxicants, and other physiological liquids of organism from blood is proposed. A patient's blood is withdrawn from an arterial blood circulatory access point, past through a polymer which removes toxicants, and re-enters the patient through a venous access point. The polymer has such a pore size and a structure which provides the removal of beta-2 microglobulin. More particularly, the pore size of the polymer is within the range 1–15 nm.

The polymers impression can be styrenic, acrylic, or any other polymers satisfying the above mentioned conditions.

One example of the material through which the blood can be passed for purification of physiological liquids of organism is a sorbent for removing toxicants from blood or plasma, which has a plurality of beads of hypercrosslinked polystyrene resin, which beads have a surface modified so as to prevent adsorption of large proteins and platelet and to minimize activation of blood complement system, without affection noticeably the accessability of the inner adsorption space of the beads for small and middle-size toxicant molecules.

To achieve the desired chemical modification of the bead surface, which are intended to enhance the hemocompatibility of the material, one possible approach is the formation of lipid-like layers on the surface of polystyrene beads, which should simulate the structure of biomembranes. Copolymers of 2-methacryloyloxyethyle-phosphorylcholine with n-butyl-methacrylate can be grafted on the surface of materials. The copolymer was shown to adsorb free phospholipids from blood to form an organized structure similar to that of a bilayer membrane. It is believed that membrane-like surfaces are thus formed which reduce adsorption of proteins and platelet from blood and make the material more biocompatible. In our approach, groups of phosphatidylcholine are formed on the surface of polystyrene beads, without a preliminary grafting of the hydrophilic copolymer suggested by Ishihara, et al.

Second approach consists of depositing heparin on the surface of the polystyrene beads. This can be done in several ways, including (i) chemical covalent binding of heparin to the polystyrene chains on the surface of beads, or (ii) electrostatic adsorption of heparin molecules, which are negatively charged, to positively charged ionogenic groups introduced into the surface layer of the beads. Heparin inhibits activation of the blood complement system and prevents formation of clots.

Still another approach consists of binding long hydrophilic polymer chains on the beads surface, which should prevent contacts between blood proteins and cells with the hydrophobic polystyrene surface.

Finally, the fourth approach is depositing high molecular weight fluorinated polyalkoxyphosphazene on the outer surface of the beads. Phosphazene represents the best biocompatible polymeric material. Modification of the sorbent surface consists in contacting the polystyrene beads with an appropriate amount of a solution of the polyphosphazene in an organic solvent. Due to the ability of the hypercrosslinked polystyrene to strongly swell with the solvent, the latter appears completely incorporated into the beads after a short period of time, whereas the dissolved polyphosphazene remains deposited on the surface of beads. The solvent incorporated into the beads is then removed by heating the beads under reduced pressure. The large size of polyphosphazene molecules used in this procedure prevents their penetration into the pores of the beads. Therefore, the whole of the internal surface of the material remains active and accessible to blood toxicants, whereas the outer surface exposes to blood proteins and cells the insoluble in water and biocompatible polyphosphazene.

The chemical modification of the surface of sorbent beads, which is the case in the first three of the above modification approaches, is facilitated by the remarkable peculiarity of the hypercrosslinked polystyrene, namely, that the reactive functional groups of the polymer are predominantly located on its surface. The hypercrosslinked polystyrene is generally prepared by crosslinking polystyrene chains with large amounts of bifunctional compounds, in particular, those bearing two reactive chloromethyl groups. The latter alkylate, in a two step reaction, two phenyl groups of neighboring polystyrene chains according to Friedel-Crafts reaction with evolution of two molecules of HC1 and formation of a cross bridge. During the crosslinking reaction, the three-dimensional network formed requires rigidity. This property gradually reduces the rate of the second step of the crosslinking reaction, since the reduced mobility of the pending second functional group of the initial crosslinking reagent makes it more and more difficult to find an appropriate second partner for the alkylation reaction. This is especially characteristic of the second functional groups which happen to be exposed to the surface of the bead. Therefore, of the pending unreacted chloromethyl groups in the final hypercrosslinked polymer, the largest portion, if not the majority of the groups, are located on the surface of the bead (or on the surface of large pores). This circumstance makes it possible to predominantly modify the surface of the polymer beads by involving the above chloromethyl groups into various chemical reactions which are subject of the present invention.

The following examples are intended to illustrate, but not to limit, the invention. In general, the examples and associated preparation protocols illustrate the modification of the surface of microporous and biporous hypercrosslinked polystyrene beads prepared by an extensive crosslinking of corresponding styrene-divinylbenzene coppolymers using monochlorodimethyl ether as the bifunctional reagent or using other conventional chloromethylation and post-crosslinking protocols. The content of residual pending chloromethyl groups in the polystyrene beads amounts to 0.5–1.0% CL for the microporous and up to 7% for biporous materials. The beads of the initial material should preferably be spherical and smooth to minimize possible damages to hematocytes.

The sorbents prepared in accordance with this invention are charged to a column or cartridge for service. The column should preferably be provided with an inlet and an outlet designed to allow easy connection with the blood circuit, and with two porous filters set between the inlet and the sorbent layer, and between the sorbent layer and the outlet. The column may be made of a biocompatible material, glass, polyethylene, polypropylene, polycarbonate, polystyrene. Of these, polypropylene and polycarbonate are preferred materials, because the column packed with the sorbent can be sterilized (e.g., autoclave and gamma-ray sterilization) before use.

The column or cartridge is then filled with a 1% solution of human serum albumin in normal saline and stored at 4° C. When ready for use, the column is washed with 0.9% NaCl solution to which has been added a suitable anticoagulant, such as ACD-A containing heparin in an effective amount. For a 250 ml cartridge, this is approximately 1l of the sodium chloride solution to which 150 ml of ACD-A containing 6,000 units of heparin has been added.

As usual the following two typical extracorporeal blood circulation systems can be employed:
  (i) Blood taken from a blood vessel of a patient is forced to pass through a column packed with the sorbent of this invention, and the clarified blood is returned to the blood vessel of the patient.
  (ii) Blood taken from a patient is first separated through a separation membrane, by centrifugation or the like into hemocytes and plasma, the plasma thus separated is then forced to pass through the column packed with the sorbent of this invention to remove toxicants from the plasma; then, the clarified plasma from the column is mixed with the hemocytes separated above, and the mixture is returned to the blood vessels of the patient.

Of these two methods, the latter is more practical because of the smaller loss of hemocytes, for example, by adhesion of platelets and erythrocytes Any other ways of performing hemoperfusion or plasma perfusion are appropriate with the modified sorbents of this invention. Especially promising seems to be the above mentioned suggestion of Bodden (U.S. Pat. No. 5,069,662, December 1991), by which high concentrations of anti-cancer agents are perfused through the liver or other body organ containing a tumor and then the effluent blood is subjected to the extracorporeal hemoperfusion to remove the excess of the drug before the blood is returned to the blood circulation system of the patient. Another perspective system is that by Shettigar, et al. (U.S. Pat. No. 5,211,850, 1993), where achieving both convective and diffusive transport of plasma across a hollow fiber membrane towards a closed chamber with a sorbent and back into the fiber channel was suggested2E. The chamber could be packed with the sorbent of this invention.

In general, the modified hypercrosslinked polystyrene sorbents of the present invention are intended to replace in hemoperfusion and plasma perfusion procedures all kinds of activated carbons. The new material is mechanically stable and does not release fines causing embolia; it is much more hemocompatible, exhibits higher sorption capacities toward a broad range of blood toxicants, and can, in principle, be regenerated and reused.

The adsorption spectrum of modified hypercrosslinked polystyrene sorbents of this invention extends to substances with molecular weights of between 100 and 20,000 daltons. The maximum adsorption is of molecules with weight of between 300 and 5,000 daltons, identified clinically as "medium molecules", which are present in abnormal quantities in ureamic and many others patients and are incompletely removed by conventional hemodialysis procedures. Such compounds as creatinine, barbiturate, phenobarbital, sodium salicylate, amphetamines, morphine sulfate, meprobamate, glutethimide, etc. can be effectively and rapidly removed from the blood using both microporous and biporous sorbents. (To avoid removal of useful drugs from blood during hemoperfusion on the new sorbents, the latter can be previously saturated with the corresponding drug to an appropriate level). In addition to removal of small and medium molecules, the biporous sorbents also shows an excellent ability to absorb cytochrom C and beta-2- microglobulin(molecular weight of about 20,000 daltons) as well as vitamin B12.

Preparation of Initial Hypercrosslinked Polystyrene

To a solution of 87.6 g xylylene dichloride (0.5 mol) in 600 ml dry ethylene dichloride 104 g (1 mol) of styrene copolymer with 0.5% divinylbenzene were added, the suspension was agitated for 1 hr and supplied with a solution of 116.8 ml tinn tetrachloride (1 mol) in 100 ml ethylene dichloride. The reaction mixture was then heated for 10 hrs at 80° C., the polymer was filtrated and carefully washed with aceton, a mixture of aceton with 0.5 N HCl, 0.5 N HCl and water until no chlorine ions were detected in the filtrate. The product dried in vacuum represented microporous hypercrosslinked polystyrene. It contained 0.65% pendant unreacted chlorine and displayed an inner surface area as high as 980 m2/g.

To a suspension of 104 g (1 mol) of a macroporous styrene copolymer with 4% divinylbenzene in 500 ml dry ethylene dichloride a solution of 76 ml (1 mol) monochlorodimethyl ether and 116.8 ml (1 mol) tinn tetrachloride (1 mol) in 100 ml ethylene dichloride was added. The mixture was then heated at 80° for 10 hrs, the polymer was filtrated and carefully washed with aceton, a mixture of aceton with 0.5 N HCl, 0.5 N HCl and water until no chlorine ions were detected in the filtrate. The product dried in vacuum represented biporous hypercrosslinked polystyrene and contained 3.88% pendent unreacted chlorine. The above extensive crosslinking resulted in the increase of its inner surface area from 120 to 1,265 m2/g.

Formation of Lipid-Like Surface Structures

EXAMPLE 1

To a dispersion of 10 g biporous polymer in 30 ml of a dioxane-methanol mixture (5:1, vol/vol) a solution of 1 g NaI and 6 ml of 2-ethanol amine in 1 ml of the same mixed solvent was added, and heated at 80° C. for 9 hrs. The polymer was filtered, washed with the dioxane-methanol mixture, methanol 0.1 N HCl (in order to protonate the secondary amino groups) and finally rinsed with water and 50 ml methanol. To the polymer, dried in vacuum, 25 ml of dry pyridine were added and then 1 ml POCl3 in 5 ml dry pyridine. The reaction mixture was kept for 15 hrs at ambient temperature, filtered, the polymer was rinsed with dry pyridine and with a solution of 1.4 g choline chloride in 25 ml dry dimethyl sulfoxide at 40° C. The mixture was heated to 60° C. for 4 hrs, kept at ambient temperature for 15 hrs, provided with 5 ml dry pyridine and, after additional 5 hrs, washed carefully with distilled water and rinsed with ethanol. The resin was kept in ethanol at 5° C. before use. Microporous hypercrosslinked polymer was modified by exactly the same procedure.

EXAMPLE 2

3 g of the biporous polymer treated with 2-ethanol amine and activated with POCl3 as described in Example 1 were treated with a solution of 0.3 g tert.-butyl-oxycarbonyl-L-serine in 2 ml dry pyridine at ambient temperature for 15 hrs, washed with ethyl acetate, dioxane, water and methanol and then dried. The protection BOC-groups were removed with trifluoroacetic acid in 1 hr at ambient temperature. The final product was washed with ether, ethanol and water. Microporous hypercrosslinked polymer was modified by exactly the same procedure.

EXAMPLE 3

4 g of the biporous hypercrosslinked polymer were allowed to swell with 16 ml of an 8% solution of NaOH in ethylene glycol and then heated to 180° C. for 5 hrs, in order to substitute the residual chloromethyl groups with ethylene glycol groups. The polymer was washed with ethanol, water, aceton and dried under vacuum. The dry polymer was then activated with POCl3 and reacted with choline chloride as described in Example 1.

Microporous hypercrosslinked polymer was modified by exactly the same procedure.

EXAMPLE 4

4 g of the biporous hypercrosslinked polymer were modified with ethylene glycol as described in Example 13, activated with POCl3 as described in Example 1 and reacted with a mixture of 3 ml glacial acetic acid and 3 ml 2-ethanol amine at ambient temperature for 3 days. The product was washed with pyridine, water and ethanol.

Microporous hypercrosslinked polymer was modified by exactly the same procedure.

Depositing Heparin on the Surface

EXAMPLE 5

The product of reacting the initial biporous polymer with 2-ethanol amine according to Example 1 was washed with 0.5 10.1 N HCl and water, provided with 5 ml of aqueous heparin solution (5,000 U/ml) and kept for 15 hrs at ambient temperature and for 4 hrs at 5° C. The polymer with the ionically absorbed heparin was filtered from the excess solution and kept in ethanol at 5° C. before use.

Microporous hypercrosslinked polymer was modified by exactly the same procedure.

EXAMPLE 6

The heparin absorbed on the polymer according to Example 5 was bonded covalently by treating the polymer for 4 hrs with an aqueous solution of glutare dialdehyde (2.0 ml of a 25% solution for 1 g of the wet polymer). The pendant aldehyde groups were coupled then with L-aspartic acid (0.2 g L-Asp in 3 ml 1 N NaOH for 1 g polymer) for 14 hrs. The polymer washed with 0.1 N NaOH and water was kept in ethanol at 5° C. before use.

Microporous hypercrosslinked polymer was modified by exactly the same procedure.

EXAMPLE 7

The heparin absorbed on the polymer according to Example 5 was bonded covalently by washing the polymer with 500 ml dry methanol, 200 ml dry dioxane and treating it for 5 hrs with a solution of 0.1 g hexamethylene diisocyanate in 3 ml dioxane (for 1 g polymer). The polymer was filtered, washed with dioxane and the pendant isocyanate groups coupled with L-aspartic acid by treating the polymer with 1 g tris-trimethylsilyl derivative of L-Asp in 3 ml heptane for 15 hrs at ambient temperature. The polymer was washed with heptane, methanol, 0.1 N NaOH and water and kept in ethanol at 5° C. before use.

Microporous hypercrosslinked polymer was modified by exactly the same procedure.

1 g of the product of reacting the initial biporous polymer with 2-ethanol amine according to Example 1 was washed with water and treated with 4 ml 25% aqueous solution of glutare dialdehyde for 5 hrs at ambient temperature. Excess of the reagent was then removed with water and the polymer was supplied with 2.5 ml of heparin solution (5,000 U/ml) for 15 hrs at ambient temperature and finally rinsed with water.

Microporous hypercrosslinked polymer was modified by exactly the same procedure.

EXAMPLE 9

1 g of the product of reacting the initial biporous polymer with 2-ethanol amine according to Example 1 was washed with methanol, dried in vacuum, swelled with dioxane and supplied with a solution of 0.1 g hexamethylene diisocyanate in 3 ml dioxane. After 10 hrs. the product was washed with dry dioxane and dimethyl sulfoxide and treated with 2.5 ml of an aqueous solution of heparin (5,000 U/ml) for 3 days. The excess heparin was removed with water and the polymer was kept in ethanol at 5° C. before use.
Microporous hypercrosslinked polymer was modified by exactly the same procedure.
Modification with Hydrophilic Polymers

EXAMPLE 10

1 g of the product of reacting the initial biporous polymer with 2-ethanol amine and activating it with glutare dialdehyde according to Example 8 was treated with 2 ml aqueous solution of 0.16 g polyethylene glycol (molecular weight 20,000) for 3 days at ambient temperature and then carefully washed with water.
Microporous hypercrosslinked polymer was modified by exactly the same procedure.

EXAMPLE 11

1 g of the product of reacting the initial biporous polymer with 2-ethanol amine and activating it with hexamethylene diisocyanate according to example 9 was treated with 2 ml aqueous solution of 0.16 g polyethylene glycol (molecular weight 20,000) for 3 days at ambient temperature and then carefully washed with water.
Microporous hypercrosslinked polymer was modified by exactly the same procedure.

EXAMPLE 12

4 g of biporous hypercrosslinked polymer was allowed to swell with 16 ml of an 8% solution of NaOH in ethylene glycol and then heated to 180° C. for 5 hrs, in order to substitute the residual chloromethyl groups with ethylene glycol groups. The polymer was washed with ethanol, water, aceton and dried under vacuum. 2 g of dry polymer, swollen with dry dioxane, were activated with hexamethylene diisocyanate as described in Example 9, washed with dry dioxane and supplied with a solution of 1.2 g polyethylene glycol (molecular weight 40,000) in 10 ml dry dimethyl sulfoxide, heated at 80° C. for 6 hrs and washed with ethanol and water.
Microporous hypercrosslinked polymer was modified by exactly the same procedure.

EXAMPLE 13

2 g of the ethylene glycol-modified polymer prepared according to Example 12 were activated with glutare dialdehyde according to the procedure described in Example 8 and treated with a solution of 1.2 g polyethylene glycol (molecular weight 40,000) in 10 ml water for 1 day at ambient temperature. The polymer was washed then with ethanol and water.
Microporous hypercrosslinked polymer was modified by exactly the same procedure.

EXAMPLE 14

To 3 g of dry biporous polymer, swollen with dry benzene, were added 15 ml of a solution containing 8 g alcoholate of polyethylene glycol (molecular weight 12,000) in dry benzene and the mixture was boiled under an argon atmosphere and adding small pieces of sodium as long as the latter dissolved in the reaction mixture (about 10 hrs). After additional two days at room temperature, the polymer was carefully washed with ethanol.
Microporous hypercrosslinked polymer was modified by exactly the same procedure.

EXAMPLE 15

According to the procedure described in Example 14, 1 g of the polymer were treated with 1 g of the alcoholate of polyethylene glycol of lower molecular weight (6,000).

EXAMPLE 16

To a solution of 0.2 g polyethylene glycol (molecular weight 12,000) in 4 ml dry benzene were added first 0.1 ml of hexamethylene diisocyanate and then, after 2 hrs, 2 g of dry biporous polymer which was previously modified with ethylene glycol according to the procedure described in Example 12.
Microporous hypercrosslinked polymer was modified by exactly the same procedure.

EXAMPLE 17

Procedure described in Example 16 was repeated with polyethylene glycol of lower molecular weight (6,000).

EXAMPLE 18

0.2 g chitosan were dissolved in 6 ml concentrated acetic acid and added to 2 g of dry biporous polymer. After 2 hrs, 10 ml of cold 30% NaOH solution were slowly added to the above mixture, the polymer was separated from the reaction mixture, rinsed with water, dehydrated with methanol, dried and heated to 80° C. with 10 ml of a solution of 0.1 g NaI in a dioxane-methanol mixture (5:1, vol/vol) for 8 hrs, in order to accomplish alkylation of the chitosan amino groups by chloromethyl groups of the polymer. The final product was washed with aqueous acetic acid and then ethanol.
Microporous hypercrosslinked polymer was modified exactly the same procedure.
Coating with Phosphazene

EXAMPLE 19

A solution of 0.0009 g poly(trifluoroethoxy) phosphazene (molecular weight $10^7$) in 8 ml ethyl acetate were added quickly to 3 g of dry biporous polymer and agitated until the whole of the solvent was totally absorbed by the polymer beads. The material was then dried under reduced pressure and washed with ethanol.

EXAMPLE 20

A solution of 130 g p-ethylstyrene, 132 g divinylbenzene (a mixture of para and metha-isomers of about 1:1) and 2.62 g benzoyl peroxide in a mixture of 600 ml toluene and 100 ml iso-amyl alcohol was suspended in 4 liters of pure water containing 1% cellulose stabilizer. After 39 in stirring at room temperature, the mixture was heated at 40° C. for 1 hours, 60° C. for 2 hours, 80° C. for 5 hours and 96° C. for 2 hours. After cooling the mixture to room temperature, the beads obtained were filtered and washed with hot water, methanol and water. The polymer was dried in oven at 80° C. within one day. 10 g of the polymer obtained were treated with a solution of 10 ml monochloridmethyl ether and 2 g ZnCl2 of 30 ml ethylene dichloride for 5 h at ambient temperature to incorporate 5,2% chlorine due to a partial chloromethylation. Thuss chlormethylated produced was in Example 1 and, finally, coated with poly(trifluorethoxy) phosphazene as described in Example 19.

The above presented description disclosed the use for purification of physiological liquids of a material which has a plurality of beads. However, other materials also can be used for this purpose, such as for example fiber materials. The fiber materials are composed of a plurality of polymer fibers with a surface modified so as to prevent adsorption of much proteins and platelet and to minimize activation of blood complement system without affection noticeably the accessibility of the inner adsorption space of the fibers for small and middle-size toxicant molecules.

It will be understood that each of the elements described above, or two or more together, may also find a useful application in other types of products and methods differing from the types described above.

While the invention has been illustrated and described as embodied in a method of and material for purification of physiological liquids of organism, and method of producing the material it is not intended to be limited to the details shown, since various modifications and structural changes may e made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A method of purification of physiological liquids of organism, comprising the step of passing a physiological liquid through a material which has a size, a shape, and a structure selected so as to remove toxic compounds from the physiological liquid and is composed of a partially chloromethylated porous highly crosslinked styrene or divinylbenzene copolymer which initially have surface exposed chloromethyl groups in which thereafter chlorine is replaced with an element which forms different surface exposed functional groups with a greater hydrophilicity and greater biocompatibility than that of the chloromethyl group, wherein the replacement step is limited exclusively to surface exposed groups.

2. A method as defined in claim 1, wherein said polymeric material has polymer beads with mainly unsubstituted hydrophobic interior which is responsible for removing of toxic compounds in a molecular range of 300 to 2000 Dalton.

3. A method as defined in claim 1, wherein said porous highly crosslinked styrene or divinylbenzene copolymer is a macroporous or mesoporous styrene-divinylbenzene-ethylstyrene copolymer subjected to a partial chloromethylation to a chlorine content of up to 7%.

4. A method as defined in claim 1, wherein said porous highly crosslinked styrene or divinylbenzene copolymer is a hypercrosslinked polystyrene produced from crosslinked styrene copolymers by an extensive chloromethylation and a subsequent post-crosslinking by treating with a Friedel-Crafts catalyst in a swollen state.

5. A method as defined in claim 1, wherein said porous highly crosslinked styrene or divinylbenzene copolymer is a hypercrosslinked polystyrene produced from crosslinked styrene copolymers by an extensive additional post-crosslinking in a swollen state with bifunctional crosslinking agents selected from the group consisting of monochlorodimethyl ether and p-xylilene dichloride.

6. A method as defined in claim 1, wherein said surface exposed functional groups of greater hydrophilicity and enhanced biocompatibility are covalently bonded or electrostatically deposited long polymeric chains selected from the group consisting of heparine, polyethyleneglycol, chitozane, and poly-bis(trifluoroethoxy)phosphazene.

7. A method as defined in claim 1, wherein said surface exposed functional groups of greater hydrophilicity and enhanced biocompatibility are covalently bonded lipid-like structures selected from a group consisting of phosphatidyl choline, phosphatidyl serine, and phosphatidyl 2-ethanol amine.

* * * * *